(12) United States Patent
Campbell et al.

(10) Patent No.: US 10,241,133 B2
(45) Date of Patent: Mar. 26, 2019

(54) PROBE TIP AND PROBE ASSEMBLY

(71) Applicant: Tektronix, Inc., Beaverton, OR (US)

(72) Inventors: Julie A. Campbell, Beaverton, OR (US); William A. Hagerup, Portland, OR (US); Ira G. Pollock, Hillsboro, OR (US); Christina D. Enns, Beaverton, OR (US); James E. Spinar, Clackamas, OR (US); Kathleen F. M. Ullom, West Linn, OR (US); Charles M. Hartmann, Forest Grove, OR (US); Daniel J. Ayres, Warren, OR (US)

(73) Assignee: Tektronix, Inc., Beaverton, OR (US)

( * ) Notice: Subject to any disclaimer, the term of this patent is extended or adjusted under 35 U.S.C. 154(b) by 0 days.

(21) Appl. No.: 15/806,270

(22) Filed: Nov. 7, 2017

(65) Prior Publication Data

US 2018/0059139 A1    Mar. 1, 2018

Related U.S. Application Data

(63) Continuation-in-part of application No. 14/676,703, filed on Apr. 1, 2015, now Pat. No. 10,119,992, and
(Continued)

(51) Int. Cl.
*H01L 21/00* (2006.01)
*G01R 1/067* (2006.01)
*H01R 13/24* (2006.01)
*C12Q 1/00* (2006.01)
*G01R 1/073* (2006.01)
(Continued)

(52) U.S. Cl.
CPC ...... *G01R 1/06722* (2013.01); *G01R 1/06733* (2013.01); *G01R 1/06766* (2013.01); *G01R 1/06772* (2013.01); *G01R 1/06788* (2013.01); *H01R 13/2421* (2013.01); *C12Q 1/00* (2013.01); *G01R 1/073* (2013.01); *G05G 1/00* (2013.01); *H01L 21/00* (2013.01);
(Continued)

(58) Field of Classification Search
CPC ....... H01L 21/00; H01L 2221/00; C12Q 1/00; C12Q 2304/00; G01R 1/00
See application file for complete search history.

(56) References Cited

U.S. PATENT DOCUMENTS 3,845,448 A * 10/1974 Hadermann ........... H01C 11/00
                                                    252/500
4,510,482 A *  4/1985 McClanahan .......... G01K 7/223
                                                    338/23
(Continued)

OTHER PUBLICATIONS

Henry W Ott, 'Balanced Differential Probe' in "Electromagnetic Compatibility Engineering", Aug. 18, 2009, pp. 698-700, John Wiley & Sons Inc., Hoboken, NJ, US.

*Primary Examiner* — Jermele M Hollington
*Assistant Examiner* — Temilade Rhodes-Vivour
(74) *Attorney, Agent, or Firm* — Kevin D. Dothager (57) ABSTRACT

A test probe tip can include a resistive element coupled with a tip component. The resistive element can include a resistive layer disposed on an exterior surface of a structural member of the resistive impedance element. In embodiments, the resistive element can be configured to form a structural component of the test probe tip without an insulating covering applied thereto. Additional embodiments may be described and/or claimed herein.

16 Claims, 6 Drawing Sheets

Related U.S. Application Data a continuation-in-part of application No. 14/587,703, filed on Dec. 31, 2014, now Pat. No. 9,810,715.

(60) Provisional application No. 62/471,947, filed on Mar. 15, 2017.

(51) Int. Cl.
*G05G 1/00* (2006.01)
*H01R 101/00* (2006.01)

(52) U.S. Cl.
CPC ...... *H01L 2221/00* (2013.01); *H01R 2101/00* (2013.01); *H01R 2201/20* (2013.01)

(56) References Cited

U.S. PATENT DOCUMENTS

| | | | | |
|---|---|---|---|---|
| 2008/0048639 A1* | 2/2008 | Sutono | ............... | G01R 1/06772 324/76.19 |
| 2008/0052028 A1* | 2/2008 | Pickerd | ............. | G01R 31/3191 702/109 |
| 2010/0060304 A1* | 3/2010 | Roland | ............. | G01R 1/06772 324/755.01 |

* cited by examiner

PROBE TIP AND PROBE ASSEMBLY

CROSS-REFERENCES TO RELATED APPLICATIONS

The present application is a continuation-in-part of U.S. Non-Provisional patent application Ser. No. 14/587,703, filed Dec. 31, 2014, entitled "HIGH IMPEDANCE COMPLIANT PROBE TIP." The present application is also a continuation-in-part of U.S. Non-Provisional patent application Ser. No. 14/676,703, filed Apr. 1, 2015, entitled "HIGH IMPEDANCE COMPLIANT PROBE TIP." In addition, the present application claims the benefit from U.S. Provisional Patent Application Ser. No. 62/471,947, filed Mar. 15, 2017, entitled "HIGH IMPEDANCE COMPLIANT PROBE TIP." All three of these related applications are incorporated herein by reference as if reproduced in their entirety.

TECHNICAL FIELD

This disclosure relates generally to test probes and, more particularly, to probe tips for test probes.

BACKGROUND

Today's engineers are attempting to test devices that carry high-speed serial busses. Many of these devices can be identified as, but are not limited to, double data rate second generation (DDR2) synchronous dynamic random-access memory (SDRAM), double data rate fourth generation (DDR4) SDRAM, and peripheral component interconnect express (PCIe). The magnitude of voltage swings and pulse frequencies are very high and the complexity of the signaling requires precise electrical probing. These and other busses are becoming highly prevalent in various types of consumer hardware devices. There are many test points of interest in each of these products.

The test points in these products vary greatly in both geometry and accessibility, usually requiring one or two points of contact. Typically, points of contact include micro traces, vias, component pads, and connector contacts that provide electrical contact with and, thus, access to high-speed signals. However, the test points are not always in the same plane and, if two probe contacts are required at once (e.g., as in the case of a differential probe), tip compliance is highly desirable to assist with positioning the probe for proper contact. Points of contact may reside on principal component analysis (PCA) hardware in virtually every angle of orientation, including from vertical to horizontal. In these types of scenarios, the test points are better accessed by probe tips with compliance.

While there are semi-permanent forms of probe contact for these access points, including the soldering or conductive epoxying of wires to these points, such solutions present a number of disadvantages, including potential damage to the device under test (DUT) during connection, long set-up times, and a requirement for exceptional dexterity skills in order to solder wires to these test points. Also, semi-permanent contacts do not provide for quick debugging. Solder-in probe tips tend to wear out after only a few connections and, thus, create a need for replacements, which can be significantly expensive. Finally, there tends to be a high variability in the signal fidelity, particularly in upper signal frequencies, due to the quality and geometry of solder and/or epoxy connections.

Accordingly, there remains a need for improved probe tips for use in connection with test probes.

DETAILED DESCRIPTION

Embodiments of the disclosed technology generally include probe tips suitable for use with a test probe and configured to provide a precise, height-compliant, quick, and light-pressure contact with a test point, e.g., on a device under test (DUT). Such a probe tip may, in some embodiments, be configured as a spring probe that includes a resistive or impedance element positioned nearly at the point of contact with the DUT. The resistive or impedance element may greatly improve the through response of the spring probe and also decrease the DUT loading significantly, thus enabling high-speed signal acquisition.

Test probes and probe tips in accordance with the disclosed technology may advantageously create a better physical and electrical control of the contact area between the components of the probe tip and also lend themselves well to fast debugging environments that typically cannot accommodate long contact setup times. Test probes and probe tips in accordance with the disclosed technology may advantageously provide superior visibility for connection placement and intuitive operation various classes of products, specifically hand-held or rapid placement probing.

Figure 1:
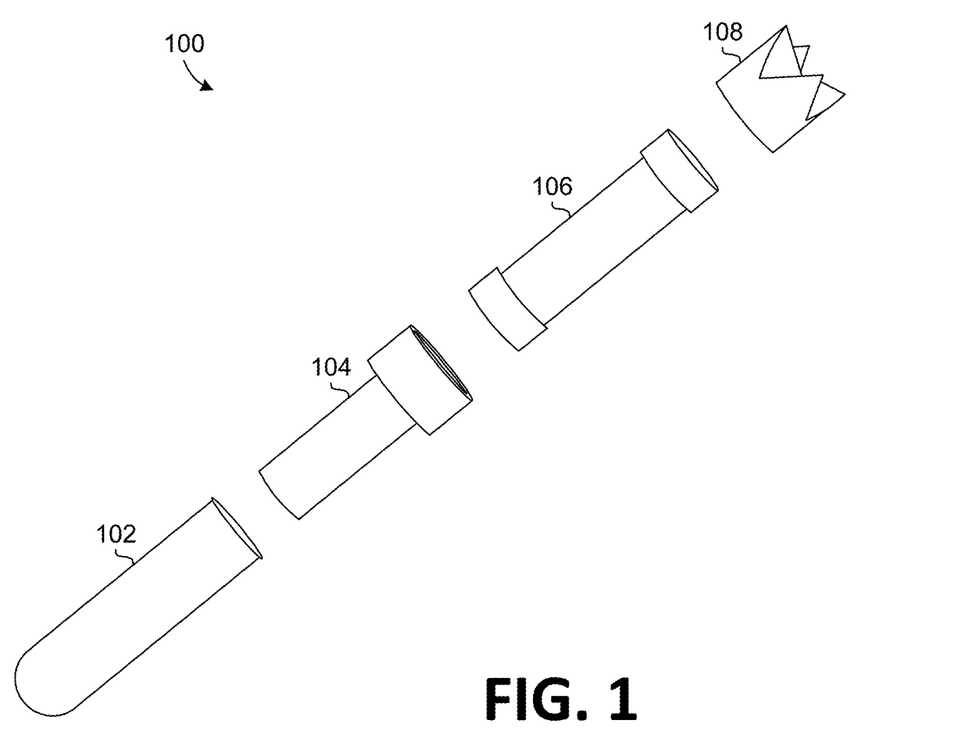
FIG. 1 illustrates an exploded view of an example of a probe tip in accordance with certain embodiments of the disclosed technology.

FIG. 1 illustrates an exploded view of an example of a test probe tip 100 in accordance with certain embodiments of the disclosed technology. In the example, the test probe tip 100 includes an optional compliance member or force deflecting assembly and a tip component 108 coupled therewith.

Figure 6:
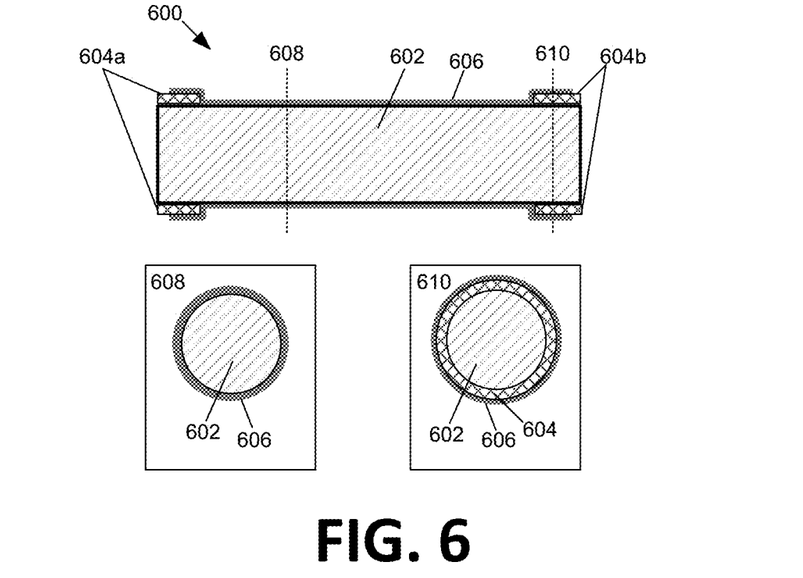
FIG. 6 is a depiction of an example round-rod resistor in accordance with various embodiments of the present disclosure.
Figure 7:
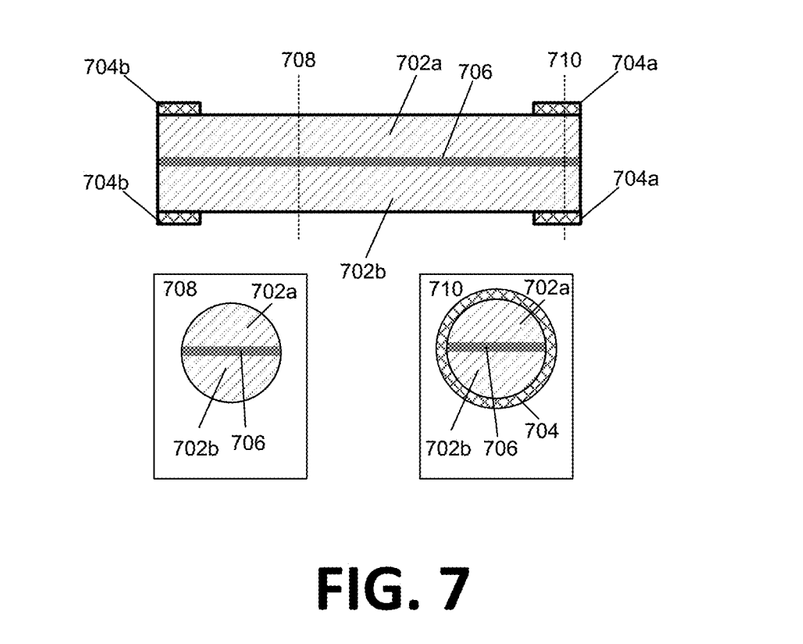
FIG. 7 is a depiction of an example round-rod resistor in accordance with various embodiments of the present disclosure.

In the example, the compliance member or force deflecting assembly includes a barrel component 102 configured to be integrated, or coupled, with a test probe. The probe tip 100 also includes a resistive element 106, e.g., a round rod resistor, and a plunger base component 104 configured to be coupled, e.g., by way of an electro-mechanical bond (e.g., solder, an electrically conductive adhesive, etc.), with an end surface of the resistive element 106. Illustrative resistive elements are depicted in FIGS. 6 and 7, below.

The resistive element 106 may, in some embodiments, have a tube-like form with resistance disposed on the outside circumference thereof. For example, the resistive element 106 may include a resistive coating, or layer, that covers a tube. In addition, to enable the electro-mechanical bond, the resistive element 106 can include metallized contacts disposed on either end of the resistive element 106. The tube-like structure of the resistor may enable high bandwidth, low bandwidth loading. The cylindrical shape of a of the depicted resistive element 106 may advantageously maximize the cross-sectional strength of the resistive element 106. It will be appreciated that, while depicted as being cylindrical, the resistive element 106 could also be implemented utilizing another suitable shape (e.g., octagonal, triangular, etc.).

In the example, the tip component 108 is configured to be coupled, e.g., by way of an electro-mechanical bond, with an end surface of the resistive element 106 opposite the end surface that is coupled with the plunger base component 104. As used herein, an electro-mechanical bond is one that provide electrical connectivity as well as structural/mechanical support. The tip component 108 may have one or more points, e.g., to establish or otherwise facilitate fine-grain electrical connectivity with one or more contact points on a DUT.

A spring mechanism may be trapped or otherwise positioned within the barrel component 102, and the plunger base 104 may be configured to slide axially inside the barrel component 102 and, consequently, be acted upon by the spring mechanism positioned inside the barrel component 102 to advantageously create a compression resistance.

Figure 2:
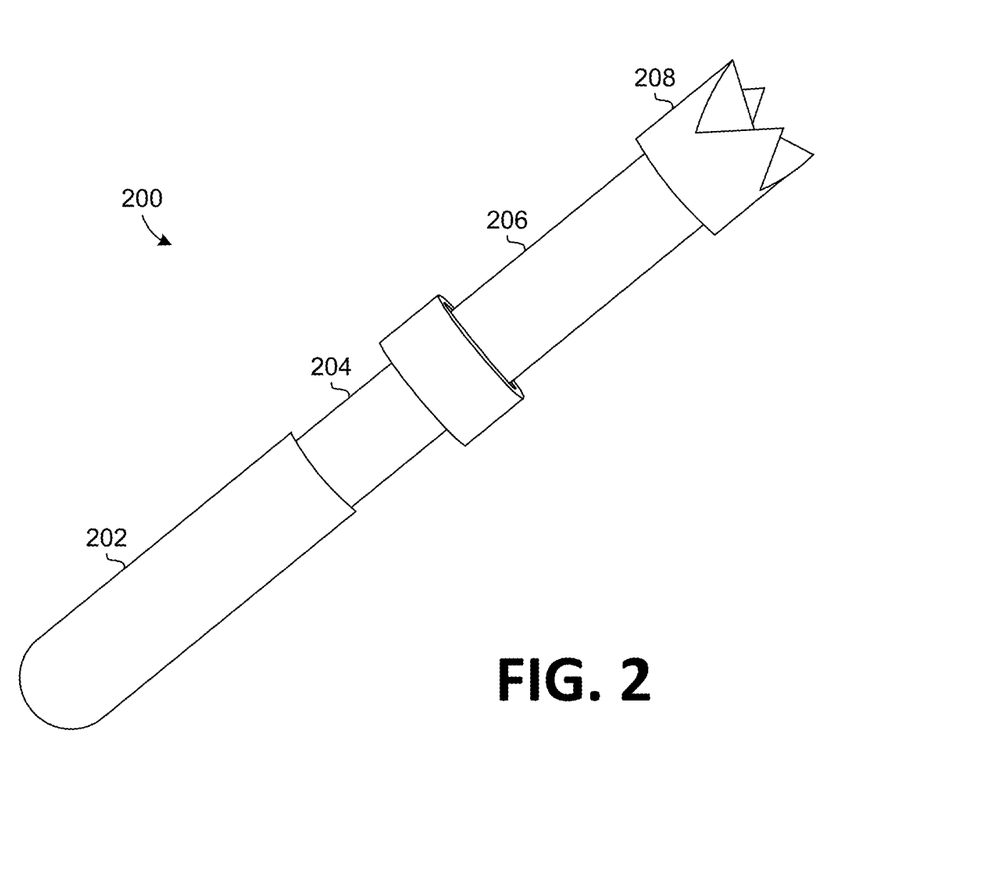
FIG. 2 illustrates an assembled view of the probe tip illustrated by FIG. 1 in accordance with certain embodiments of the disclosed technology.

FIG. 2 illustrates an assembled view of an example of a test probe tip 200 having an optional compliance member or force deflecting assembly and a tip component coupled therewith in accordance with certain embodiments of the disclosed technology. In the example, a barrel component 202 receives a plunger base 204 that is coupled, e.g., by way of an electro-mechanical bond, with an end of a resistive element 206. The resistive element 206 may have a tube-like form with resistance on the outside circumference thereof. In the example, a tip component 208 is coupled, e.g., by way of an electro-mechanical bond, with an end of the resistive element 206 opposite the end thereof that is coupled with the plunger base 204.

As with the test probe tip 100 illustrated by FIG. 1, a spring mechanism may be trapped or otherwise positioned within the barrel component 202, and the plunger base 204 may be configured to slide axially inside the barrel component 202 and be acted upon by the spring mechanism therein to advantageously create a compression resistance.

Figure 3:
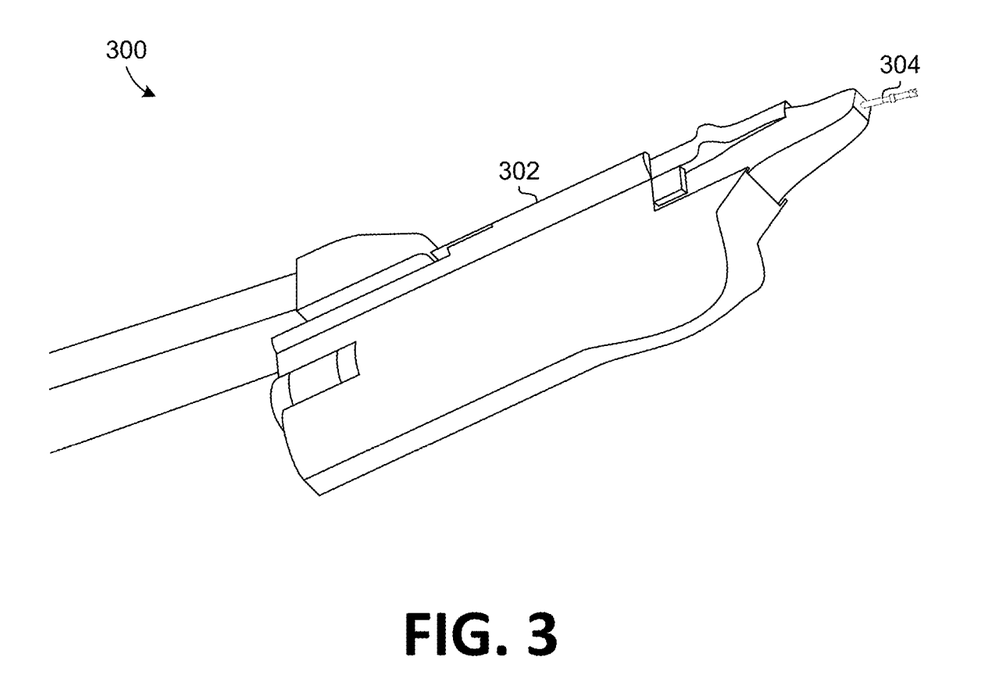
FIG. 3 illustrates an example of a single-tip test probe in accordance with certain embodiments of the disclosed technology.

FIG. 3 illustrates an example of a single-tip test probe 300 in accordance with certain embodiments of the disclosed technology. In the example, the test probe 300 includes a test probe body 302 and a test probe tip 304, such as the test probe tips 100 and 200 illustrated by FIGS. 1 and 2, respectively. A user may use the test probe 300 to create a compression resistance between the test probe tip 304 and a test point, such as a high-speed signal access point or other suitable point on a DUT, for example.

Figure 4:
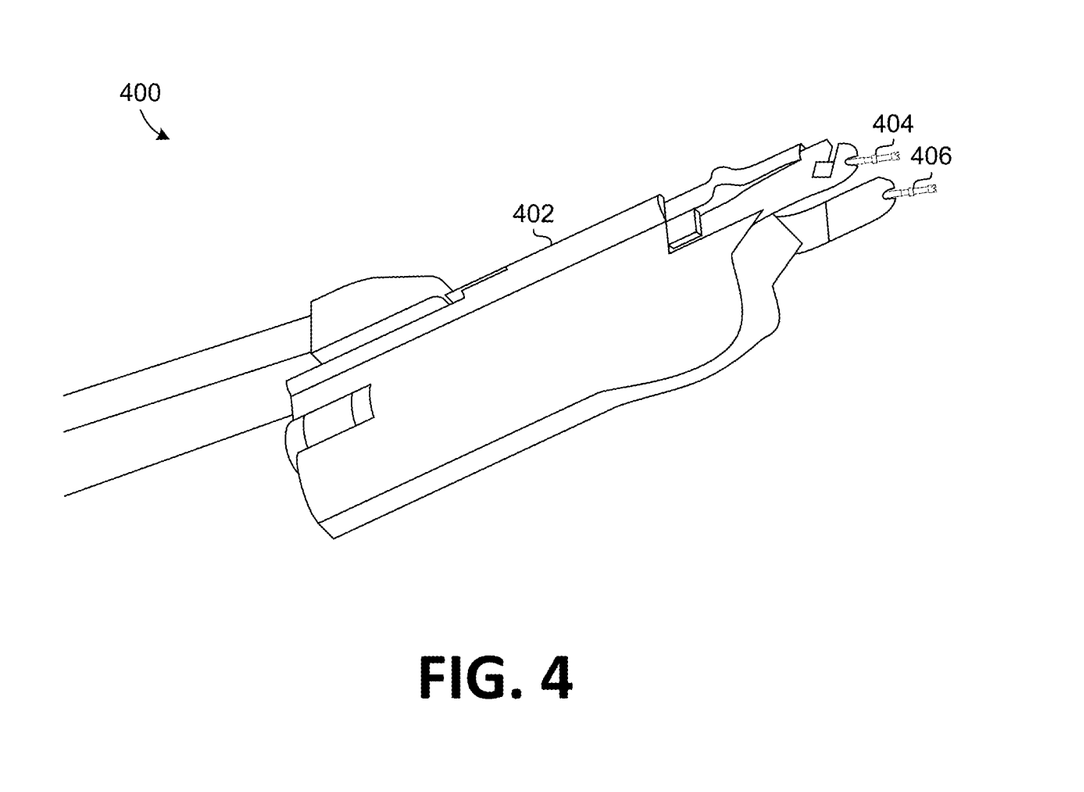
FIG. 4 illustrates an example of a differential probe in accordance with certain embodiments of the disclosed technology.

FIG. 4 illustrates an example of a differential probe 400 in accordance with certain embodiments of the disclosed technology. In the example, the differential probe 400 includes a probe body 402 and two test probe tips 404 and 406, such as the test probe tips 100 and 200 illustrated by FIGS. 1 and 2, respectively. A user may use the differential probe 400 to create a compression resistance between either or both of the test probe tips 404 and 406 and one or two test points, such as a high-speed signal access point or other suitable point on a DUT, for example.

Figure 5:
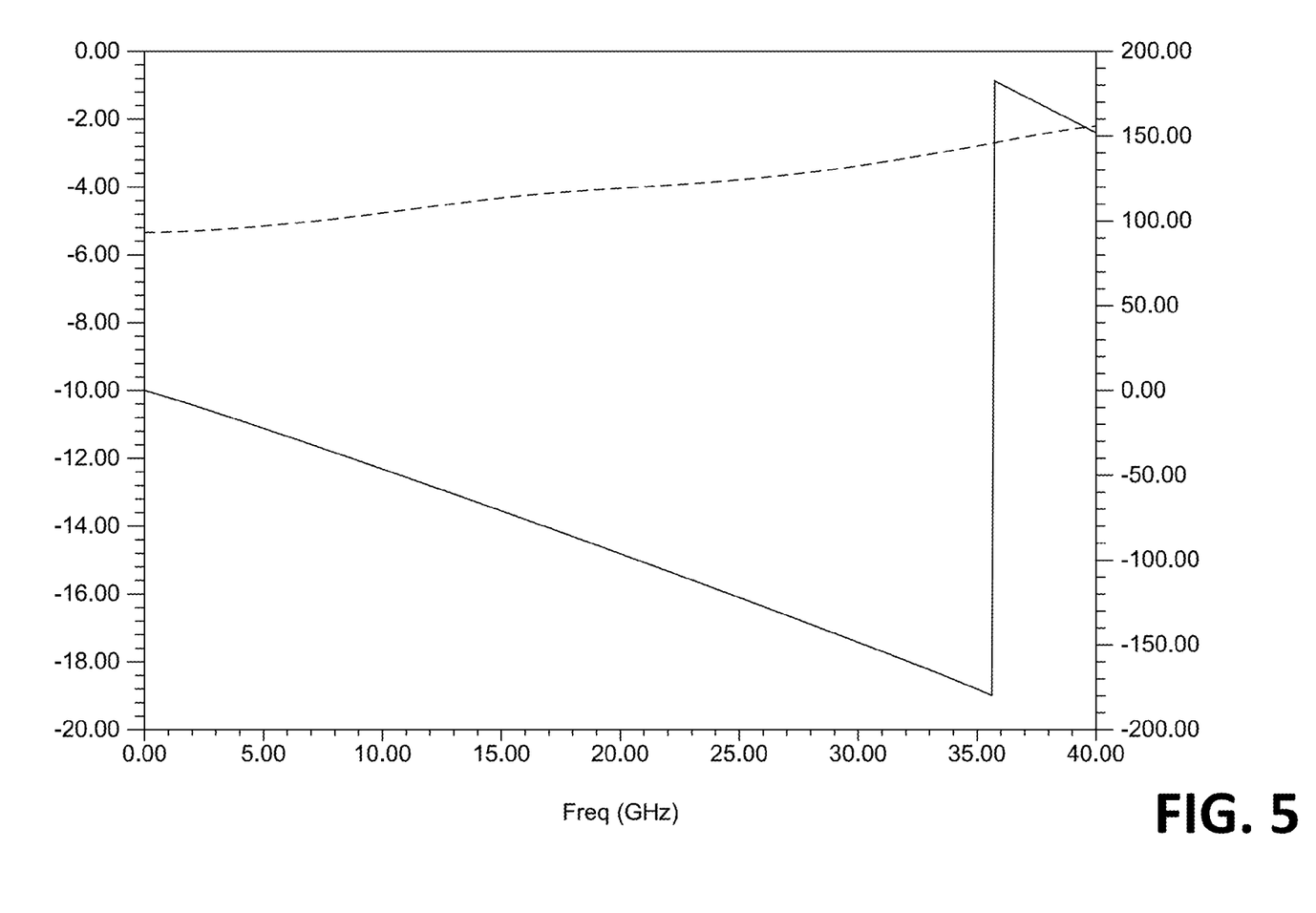
FIG. 5 is a graphical representation of an example of a frequency response plot for a test probe tip in accordance with certain embodiments of the disclosed technology.

FIG. 5 is a graphical representation of an example of a frequency response plot 500 for a test probe tip in accordance with certain embodiments of the disclosed technology. The configuration of the resistor fabrication (e.g., rod tube nature) and close proximity to the contact point of the DUT contact generates a highly flat response to signals on the DUT, yielding high signal reproduction fidelity while keeping DUT loading to a minimum. This is important for measuring signal busses that are sensitive to loading. If the tip/probe input structure loads (e.g., reduces or alters the signal eye) the signaling between transmitter-receiver is interrupted, the communication bus under test fails to work properly, which ruins the test. Probe tips in accordance with the disclosed technology advantageously limits this issue greatly.

FIG. 6 is a depiction of a length-wise cross-section and two width-wise cross-sections along lines 608 and 610, depicted in the boxes with similar numbering of an example resistor 600, in accordance with various embodiments of the present disclosure. As depicted, the resistor includes a structural member 602, a metallic layer 604a and 604b disposed around a circumference of either end of structural member 602, and a resistive layer 606 disposed on an exterior surface of the round rod resistor.

Structural member 602 is composed of material that provides sufficient structural rigidity and sufficient strength to withstand the stresses of probing without breaking. As such, structural member 602 can prevent the need for resistor 600 to be embedded in an encapsulation material. This can be beneficial, because encapsulating the resistor in an encapsulation material, such as, for example, plastic, can have adverse effects on the flatness of the frequency response of the resulting probe tip. To help maintain the flatness of the frequency response, it can be desirable to have the only insulating material surrounding resistor 600 be air, which is enabled, at least in part, by structural member 602. Materials providing sufficient structural rigidity and sufficient strength can vary based on the intended use of the probe tip, but can include zirconium, quartz, or any combination of these. It will be appreciated that these materials are merely meant to be illustrative of possible material and that other possible materials will be readily discernible to a person of ordinary skill in the art. In addition, while structural member 602 is depicted as generally being cylindrical in nature, it will be appreciated that other shapes (e.g., octagonal, triangular, etc.) can be utilized without departing from the scope of this disclosure Metallic layer 604a and 604b can include any suitable material for making an electrical connection with plunger base component 104 and tip component 108. Such materials can include, silver, gold, copper, or any other suitably electrically conductive material, or combinations of any of these. Metallic layer 604a and 604b can be applied utilizing any suitable process, such as a micropenning process, or any other suitable process. The metallic layers can be formed as caps, or could be formed to leave either end of the structural member exposed.

Resistive layer 606 can be a thick film resistive layer. This film can be applied through a micropenning process (e.g., resistive ink, such as that available from Ohmcraft), flat screened, or any other suitable process. Resistive layer 606 can include, for example, oxides of ruthenium, iridium and/or rhenium, or any other suitable material. Resistive layer 606 can be applied to contact metallic layer 604a and 604b either on a surface of the metallic layers or between the metallic layers and the structural member 602. In addition, resistive layer, or any other layer for that matter, may be laser cut for additional precision or to adjust an amount of resistance (e.g., by removing portions of the resistive layer) for the resistor.

FIG. 7 is another depiction of a length-wise cross-section and two width-wise cross-sections along lines 708 and 710, depicted in the boxes with similar numbering of an example resistor 700, in accordance with various embodiments of the present disclosure. As depicted, the resistor includes semi-cylindrical structural members 702a and 702b, a metallic layer 704a and 704b disposed around a circumference of either end of structural member 702, and a resistive layer 706 disposed between structural members 702a and 702b.

Structural members 702a and 702b are composed of material that provides sufficient structural rigidity and sufficient strength to withstand the stresses of probing without breaking. As such, structural member 702 can prevent the need for resistor 700 to be embedded in an encapsulation material. This can be beneficial, because encapsulating the resistor in an encapsulation material, such as, for example, plastic, can have adverse effects on the flatness of the frequency response of the resulting probe tip. To help maintain the flatness of the frequency response, it can be desirable to have the only insulating material surrounding resistor 700 to be air, which is enabled, at least in part, by structural member 702. Materials providing sufficient structural rigidity and sufficient strength can vary based on the intended use of the probe tip, but can include zirconium, quartz, or any combination including one or more of these. It will be appreciated that these materials are merely meant to be illustrative of possible material and that other possible materials will be readily discernible to a person of ordinary skill in the art.

Metallic layer 704a and 704b can include any suitable material for making an electrical connection with plunger base component 104 and tip component 108. Such materials can include, silver, gold, copper, or any other suitably electrically conductive material, or combinations of any of these. Metallic layer 704a and 704b can be applied utilizing any suitable process, such as a micropenning process, or any other suitable process. The metallic layers can be formed as caps, or could be formed to leave either end of the structural member exposed.

Resistive layer 706 can be a thick film resistive layer. This film can be applied through a micropenning process (e.g., resistive ink, such as that available from Ohmcraft), flat screened, or any other suitable process. Resistive layer 706 can include, for example, oxides of ruthenium, iridium and/or rhenium, or any other suitable material. Resistive layer 606 can be applied to contact metallic layer 604a and 604b either on a surface of the metallic layers or between the metallic layers and the structural member 602. In addition, resistive layer, or any other layer for that matter, may be laser cut for additional precision or to adjust an amount of resistance (e.g., by removing portions of the resistive layer) for the resistor.

Having described and illustrated the principles of the invention with reference to illustrated embodiments, it will be recognized that the illustrated embodiments may be modified in arrangement and detail without departing from such principles, and may be combined in any desired manner. And although the foregoing discussion has focused on particular embodiments, other configurations are contemplated.

In particular, even though expressions such as "according to an embodiment of the invention" or the like are used herein, these phrases are meant to generally reference embodiment possibilities, and are not intended to limit the invention to particular embodiment configurations. As used herein, these terms may reference the same or different embodiments that are combinable into other embodiments.

Consequently, in view of the wide variety of permutations to the embodiments that are described herein, this detailed description and accompanying material is intended to be illustrative only, and should not be taken as limiting the scope of the invention. What is claimed as the invention, therefore, is all such modifications as may come within the scope and spirit of the following claims and equivalents thereto.

What is claimed is:

1. A test probe tip, comprising:
a resistive element having a structural member with a resistive layer applied to an exterior surface of the structural member, wherein the resistive layer is disposed lengthwise along the structural member to electrically couple a first end of the structural member with a second end of the structural member; and
a tip component configured to be coupled with the first end of the resistive element, wherein the resistive element is configured to be coupled with the tip component such that the resistive element forms a structural component of the test probe tip without an insulating covering applied thereto, and wherein the resistive layer is configured to electrically couple the tip component with a test probe body.

2. The test probe tip of claim 1, wherein the structural member of the resistive element further includes zirconium, quartz, or a combination thereof.

3. The test probe tip of claim 1, wherein the resistive layer comprises oxides of ruthenium, iridium, and/or rhenium.

4. The test probe tip of claim 1, wherein the structural member is substantially cylindrical in shape.

5. The test probe tip of claim 1, further comprising a force deflecting assembly coupled with the resistive element.

6. The test probe tip of claim 5, wherein the force deflecting assembly is configured to couple the test probe tip to the test probe body.

7. The test probe tip of claim 5, wherein the force deflecting assembly includes:
a plunger component configured to be coupled with the second end of the resistive element, and wherein the resistive layer electrically couples the tip component with the plunger component;
a barrel component configured to receive the plunger component, wherein the plunger component is configured to slide axially inside the barrel component; and
a spring mechanism positioned within the barrel component and configured to act on the plunger component responsive to the plunger component sliding in an inward direction inside the barrel component.

8. The test probe tip of claim 7, wherein the spring mechanism is configured to create a compression resistance between the probe tip and a test point on a device under test (DUT).

9. A test probe, comprising:
a test probe body configured to be coupled with a test and measurement device; and
a test probe tip, coupled with the test probe body, configured to be coupled with a device under test, the test probe tip including:
a resistive element having a structural member with a resistive layer applied to an exterior surface of, wherein the resistive layer is disposed lengthwise along the structural member to electrically couple a first end of the structural member with a second end of the structural member; and a tip component configured to be coupled with the first end of the resistive element such that the resistive element forms a structural component of the test probe tip without an insulating covering applied thereto, and wherein the resistive layer is configured to electrically couple the tip component with the test probe body.

10. The test probe of claim 9, wherein the structural member of the resistive element includes zirconium, quartz, or a combination thereof.

11. The test probe of claim 9, wherein the resistive layer comprises oxides of ruthenium, iridium, and/or rhenium.

12. The test probe of claim 9, wherein the structural member is substantially cylindrical in shape.

13. The test probe of claim 9, wherein the test probe tip further comprises a force deflecting assembly coupled with the resistive element.

14. The test probe of claim 13, wherein the force deflecting assembly couples the test probe tip to the test probe body.

15. The test probe of claim 14, wherein the force deflecting assembly includes:

a plunger component configured to be coupled with the second end of the the resistive element, and wherein the resistive layer electrically couples the tip component with the plunger component;

a barrel component configured to receive the plunger component, wherein the plunger component is configured to slide axially inside the barrel component; and a spring mechanism positioned within the barrel component and configured to act on the plunger component responsive to the plunger component sliding in an inward direction inside the barrel component.

16. The test probe of claim 15, wherein the spring mechanism is configured to create a compression resistance between the probe tip and a test point on a device under test (DUT).

\* \* \* \* \*